US008110721B2

(12) United States Patent
Wiles et al.

(10) Patent No.: US 8,110,721 B2
(45) Date of Patent: *Feb. 7, 2012

(54) METHODS FOR MAINTAINING GENETIC STABILITY OF INBRED ANIMAL STRAINS

(75) Inventors: Michael V. Wiles, Mount Desert, ME (US); Robert Taft, Southwest Harbor, ME (US); Eva M. Eicher, Seal Cove, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 30 days.

This patent is subject to a terminal disclaimer.

(21) Appl. No.: 12/536,909

(22) Filed: Aug. 6, 2009

(65) Prior Publication Data

US 2010/0095389 A1   Apr. 15, 2010

Related U.S. Application Data

(63) Continuation of application No. 10/915,840, filed on Aug. 11, 2004, now Pat. No. 7,592,501.

(60) Provisional application No. 60/497,451, filed on Aug. 22, 2003.

(51) Int. Cl.
  *A01K 67/027* (2006.01)
  *A01K 67/00* (2006.01)
  *C12N 15/00* (2006.01)
(52) U.S. Cl. ................. 800/22; 800/8; 800/18
(58) Field of Classification Search .............. 800/3, 8, 800/18
  See application file for complete search history.

(56) References Cited

U.S. PATENT DOCUMENTS

| 5,160,312 | A | 11/1992 | Voelkel |
| 5,758,763 | A | 6/1998 | Sanda |
| 2002/0131957 | A1 | 9/2002 | Gavin |
| 2008/0026361 | A1 | 1/2008 | Ostermeier et al. |

FOREIGN PATENT DOCUMENTS

| WO | WO 97/37009 | 10/1997 |
| WO | WO 00/04186 | 1/2000 |
| WO | WO 00/11147 | 3/2000 |
| WO | WO 01/84920 | 11/2001 |

OTHER PUBLICATIONS

Ueda et al., 1995, J. Reproduction and Development, vol. 41(3), pp. 181-186.*
Sztein et al., 2001, Cryobiology, vol. 41 pp. 28-39.*
Prelle, 1999, Cell Tissues Organs, vol. 165, pp. 220-236.*
Moreadith, 1997, J. Mol. Med., vol. 75 pp. 208-216.*
Denning, 2003, Reproduction, vol. 126, pp. 1-11.*
Smith, 2002, Journal of Biotechnology, vol. 99, pp. 1-22.*
Bailey, Donald, W., "Sources of Subline Divergence and their Relative Importance for Sublines of Six Major Inbred Strains of Mice", *Origins of Inbred Mice*. The Jackson Laboratory, Aug. 13, 2007 http://www.informatics.jax.org/morsebook/frames/frame15.shtml.
Bailey DW, "How pure are inbred strains of mice?", 1982, vol. 8, pp. 210-214.
Bailey DW, "Genetic Drift: the problem and its possible solution by frozen-embryo storage", 1977, Ciba Found Symp., pp. 291-303.
Butler, L. et al., "Genetic analysis of the BB/W diabetic rat", Can J. Genet. Cytol. 25:7-15 (1983).
Byers, Shannon L. et al., Performance of ten inbred mouse strains following assisted reproductive technologies (ARTs), Theriogenology 65 (2006) 1716-1726.
Candy, C.J., et al., "Restoration of a normal reproductive lifespan after grafting of cryopreserved mouse ovaries", Human Reproduction, 15(6):1300-1304 (2000).
Chiu, T.T.Y., et al., "Effects of myo-inositol on the in-vitro maturation and subsequent development of mouse oocytes," Human Reproduction, 18(2):408-416(2003).
Cseh, S., "Vitrification of mouse embryos in two cryoprotectant solutions", 1999, Theriogenology, vol. 52, pp. 103-113.
Eggan, K., et al., "Male and female mice derived from the same embryonic stem cell clone by tetraploid embryo complementation", Nature Biotechnology, 20:455-459 (2002).
Hirabayahsi et al., 1997, Exp. Anim., vol. 46, No. 2, pp. 111-115.
Huang, Kuo-Yu et al., "Functionality of cryopreserved juvenile ovaries from mutant mice in different genetic background strains after allotransplantation", Cryobiology (2009), doi:10.1016/j.cryobiol.2009.10.003.
Hubner, K., et al., "Derivation of Oocytes from Mouse Embryonic Stem Cells", Science, 300:1251-1256 (2003).
Johnson, K.R., et al., "A Major Gene Affecting Age-Related Hearing Loss is Common to at Least Ten Inbred Strains of Mice", Genomics, 70:171-180 (2000).
Ehling et al., "*Genetic structure and diversity of the gene reserve of the old type German Black Pied cattle*," (Zuchtungskunde, vol. 71, issue 2, Abstract, 1999).
Pisenti et al., "*Avian Genetic Resources at Risk*,", (Genetic Resources Conservation Program, Div. Agri and Nat Res, UC Davis, Report No. 20, Sep. 1999).
Kimura, Y., et al., "Mouse oocytes injected with testicular spermatozoa or round spermatids can develop into normal offspring," Development, 121:2397-2405 (1995).

(Continued)

*Primary Examiner* — Peter Paras, Jr.
*Assistant Examiner* — David A Montanari
(74) *Attorney, Agent, or Firm* — Wolf, Greenfield & Sacks, P.C.

(57) ABSTRACT

The present invention provides novel methods of maintaining genetic stability of non-human animal inbred strains. In the methods, pedigree-tracked cryopreserved embryos derived from a foundation colony are produced and used to re-establish the foundation colony at appropriate intervals.

16 Claims, 1 Drawing Sheet

OTHER PUBLICATIONS

Kubota, H., et al., "Spermatogonial stem cells share some, but not all, phenotypic and functional characteristics with other stem cells", PNAS, 100(11):6487-6492 (2003).

Liu, J., "Fertilization of mouse oocytes from in vitro-matured preantral follicles using classical in vitro fertilization or intracytoplasmic sperm injection", 2002, Biology of Reproduction, vol. 67, pp. 575-579.

Mobraaten, LE., 1986, J. In Vitro Fert. Embryo Transfer, vol. 3, No. 1, pp. 28-32.

Nagy, A., et al., "Derivation of completely cell culture-derived mice from early-passage embryonic stem cells", Proc. Natl. Acad. Sci., 90:8424-8428 (1993).

Nakagata K., "Cryopreservation of mouse spermatozoa", Mammalian Genome, vol. 11, pp. 572-576.

Nomura et al., "Establishment and Preservation of Reference Inbred Strains of Rats for General Purpose Use: Report on U.S.—Japan non-Energy Research and Development Cooperation: Laboratory Animal Science", ILAR Journal Online 33(3):1-3 (1991).

O'Brien, M.J., et al., "A Revised Protocol for In Vitro Development of Mouse Oocytes from Primordial Follicles Dramatically Improves Their Developmental Competence", Biology of Reproduction, 68:1682-1686 (2003).

Ostermeier, G. Charles et al., "Conserving, Distributing and Managing Genetically Modified Mouse lines by Sperm Cryopreservation", PLoS ONE, Jul. 2008, vol. 3, Issue 7, pp. 1-8.

Sato, M., et al., "Comparison of Intrabursal Transfer of Spermatozoa, A New Method for Artificial Insemination in Mice, With Intraoviductal Transfer of Spermatozoa", Journal of Assisted Reproduction and Genetics, 19(11):523-530(2002).

Specht, C.G., et al., "Deletion of the alpha-synuclein locus in a subpopulation of C57BL/6J inbred mice", BMC Neuroscience, 2:11 (2001).

Sztein, J., et al., "Cryopreservation and Orthotopic Transplantation of Mouse Ovaries: New Approach in Gamete Banking", Biology of Reproduction, 58:1071-1074 (1998).

Sztein, J.M., et al., "Comparison of Permeating and Nonpermeating Cryoprotectants for Mouse Sperm Cryopreservation", Cryobiology, 41:28-39 (2001).

Taft, Robert A. et al., "Know thy Mouse", TRENDS in Genetics (2006), doi:10.1016/j.tig.2006.09.010.

Toyooka, Y., et al., "Embryonic stem cells can form germ cells in vitro", 100(20):11457-11462 (2003).

Ueda, O., "Factors affecting the efficiency of chimera production by coculture of zona-free embryos with frozen-thawed embryonic stem cells in mice", 1995, J. Reprod. Dev., vol. 41, pp. 181-186.

Wotjak, C.T., "C57Black/Box? The importance of exact mouse strain nomenclature",Trends in Genetics, 19(4):183-184 (2003).

\* cited by examiner

Figure. Generating embryos derived from a foundation colony to be used for maintaining genetic stability of an inbred strain.
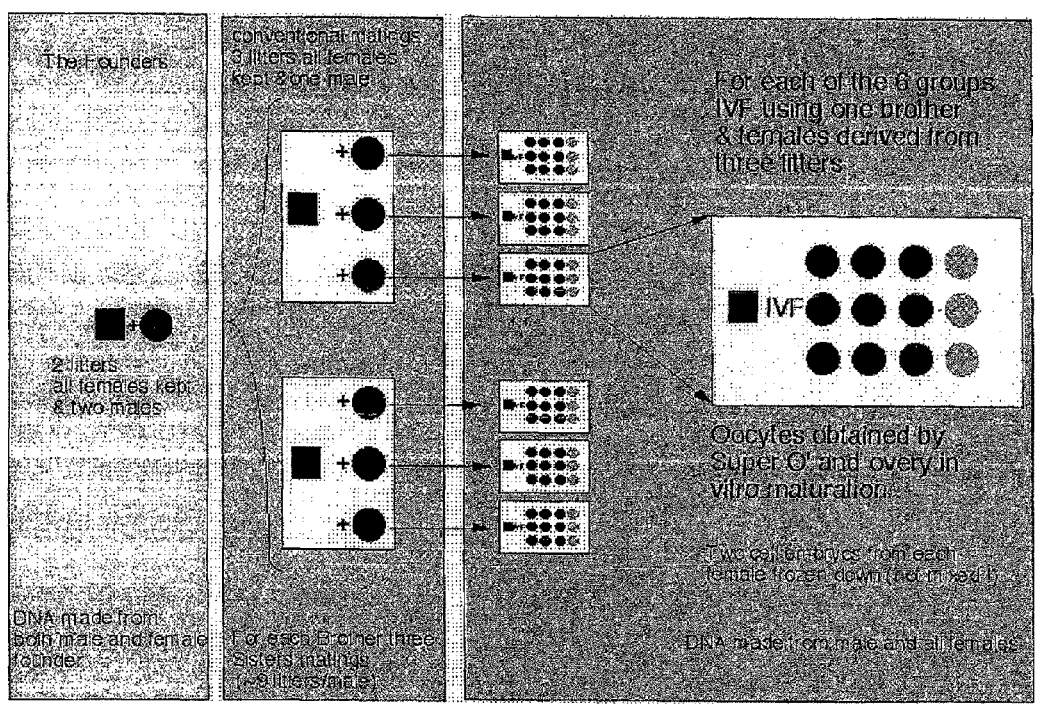

METHODS FOR MAINTAINING GENETIC STABILITY OF INBRED ANIMAL STRAINS

CROSS-REFERENCE TO RELATED APPLICATIONS

The present application is a continuation of U.S. application Ser. No. 10/915,840, filed Aug. 11, 2004, now U.S. Pat. No. 7,592,501, which claims the benefit under U.S.C. §119 of U.S. Provisional Application No. 60/497,451, filed Aug. 22, 2003; the specification of each referenced application is incorporated by reference in its entirety.

GOVERNMENTAL FUNDING

This invention was made with government support under Grant No. GM020919 awarded by the National Institutes of Health. The government has certain rights in the Invention.

BACKGROUND OF THE INVENTION

Experimental animals serve as useful models for studying human diseases. Advances in transgenic and targeted mutation technology have made the mouse not only a successful surrogate organism for human genome analysis, but also the most valuable model system to investigate the genetics and pathogenesis of human diseases. The valid interpretation of experimental results obtained from mouse studies depends upon the assurance that the mouse models used are genetically pure and well defined. For this reason, researchers have traditionally used inbred strains for experiments, because these mice, in contrast to outbred mouse stocks, offer uniformity and constancy of genotypes. Mice of inbred strains can be repeatedly accessed as homogeneous experimental individuals, with predictable phenotypes and defined allelic composition.

The constancy of genotype in inbred strain mice, however, is never fully realized because both new mutations arise and gradually accumulate together with continual allele fixation of residual heterozygosity. These changes in genotype within inbred mice is known as genetic drift. At each generation, there is a likelihood of spontaneous new mutations arising. These mutations first occur as heterozygous mutations. When both founders of an inbred strain, by chance, become homozygous for a spontaneous mutation, this mutation becomes fixed in the inbred strain, and all later generations of this inbred mouse strain will carry this mutation.

Genetic drift as a result of the rise of spontaneous mutations will impact genetic analysis performed on animals derived from an inbred strain. The valid interpretation of experimental data generated using inbred animals is undermined by genetic drift. A recent publication illustrates this point. In 2001, Specht and Schoepfer discovered a chromosomal deletion in C57BL/6JOlaHsd mice (See Specht and Schoepfer, Deletion of the alpha-synuclein locus in a sub-population of C57BL/6J inbred mice, BMC Neurosci. 2, 11 (2001). The mutation was the ablation of the more than 79 kb of the alpha-synuclein locus. This gene encodes a presynaptic telencephalic protein that has been implicated in the etiology of Parkinson and Alzheimer diseases. Many researchers have used C57BL/6JOlaHsd mice as a wild-type control for their experiments or to backcross with other mutations, unaware of this problem. Now their experimental results need to be re-evaluated in light of the alpha-synuclein deletion present in the strain. See Wotjak, C57Black/Box? The importance of exact mouse strain nomenclature, Trends in Genetics 19: 183-184 (2003).

Moreover, researchers frequently need to compare data obtained from inbred animals over extended periods of time. Due to the effects of genetic drift, over time, inbred strain mice become genetically different from the "same" inbred mice at an earlier point in time. The longer the time span, the more likely a genetic differences will accumulate and become fixed. The existence of genetic drift thus undermines one's ability to carry out valid comparisons across extended periods of time.

For these reasons it is desirable to reduce genetic drift in inbred animal strains and maintain their genetic stability over protracted periods of time. There is a pressing need in the art for methods of maintaining genetic stability of inbred animal strains. Such methods are provided herein.

SUMMARY OF THE INVENTION

The present invention provides novel methods of maintaining genetic stability of non-human animal inbred mouse strains. Currently, a pedigreed foundation colony is maintained for an inbred mouse strain. The foundation colony of an inbred mouse strain is derived from a single brother-sister mating. Two to four times a year, a new brother-sister pair is selected from the foundation colony as the new founder pair to re-establish the colony. Using this approach, a foundation colony today will be genetically different from the foundation colony years from now, because of the accumulation of spontaneous mutations and allele fixation in the inbred mouse strain over time.

Applicants have devised novel methods of limiting genetic drift and maintaining genetic stability of inbred mice by producing a pedigree-tracked stock of cryopreserved embryos derived from a foundation colony and using the stock to re-establish the foundation colony at appropriate intervals. Having a cryopreserved stock as a repository for the foundation colony and periodically re-establishing the foundation colony using the cryopreserved stock reduces the numbers of generations passed for a given time period and thus effectively reduces the effective rate of genetic drift. Because the pedigree of each embryo in the stock is known, one can selectively recover only embryos that are brother-sister pairs. As a result, the inbred mouse strain is propagated through consecutive brother-sister breeding, keeping the inbred status of the mouse strain intact. This process can be repeated at appropriate intervals, thus allowing one to maintain an inbred mouse strain with limited genetic drift without affecting the inbred status of the strain.

A pedigree-tracked stock of cryopreserved embryos is produced by obtaining and cryopreserving embryos from a brother-sister pair derived from a foundation colony. Embryos may be obtained by breeding the brother-sister pairs. Embryo production may be by mating (copulation) or by in vitro or in vivo artificial means. Artificial means include, but are not limited to, artificial insemination, in vitro fertilization of in vitro or in vivo matured oocytes, embryo transfer, intracytoplasmic sperm injection, cloning, in vitro culture of fertilized oocytes and embryo splitting, and the like.

The pedigree-tracked cyropreserved stock may also be a stock of embryonic stem cells, a stock of gametes, or a stock of pre-gametes. Gametes, pre-gametes or embryonic stem cells are derived from a foundation colony of inbred mouse strain. Such cryopreserved stocks can be used as frozen repositories for a foundation colony to maintain genetic stability of an inbred strain. The present invention provides methods of producing pedigree-tracked cryopreserved stock and methods of using the stock to maintain genetic stability of an inbred strain.

The present invention also provides pedigree-tracked stocks of cyropreserved non-human animal embryos, gametes, pre-gametes, or embryonic stem cells. Each of these stocks is derived from a foundation colony of an inbred strain. The pedigree of the respective embryos, gametes, pre-gametes or embryonic stem cells for each strain is tracked and recorded to permit selective recovery at a future time.

Applicants further provide genetically stabilized non-human animal inbred mouse strains that are made by the methods described herein. A non-human animal may be a rodent, such as a rat or a mouse.

Applicants further provide methods for conducting a business of supplying genetically stabilized non-human animal inbred strains. According to the present invention, a foundation colony is maintained for an inbred strain, and a pedigree-tracked cryopreserved stock of embryos derived from the foundation colony is produced. At appropriate intervals, a pair of brother-sister embryos derived from a single brother-sister pair are selected and live animals are produced from the sibling embryos. A brother-sister pair is selected from the animals produced and is used as a new founder pair to re-establish the foundation stock. In response to a customer's request, one or multiple animals of the genetically stabilized inbred mouse strain are supplied to the customer.

Practice of these methods makes it possible to maintain an inbred strain with limited genetic drift without affecting the inbred status of the strain. As a result, inbred animals that are truly genetically uniform with well-defined genotypes over an extended period of time will be available to animal researchers, greatly aiding valid data interpretation and meaningful data comparison.

BRIEF DESCRIPTION OF THE DRAWING

The FIGURE shows a scheme to generate sufficient numbers of pedigree-tracked embryos derived from a foundation colony to produce pedigree-tracked cyropreserved embryos for maintaining genetic stability of an inbred strain.

DETAILED DESCRIPTION OF THE INVENTION

The present invention provides novel methods of maintaining genetic stability of non-human animal inbred strains. As described herein, the genetic stability of an inbred animal strain is maintained by producing pedigree-tracked cryopreserved embryos derived from a foundation colony and using these to re-establish the foundation colony at appropriate intervals. Practice of the methods reduces the numbers of generations passed for a given time period and thus reduces the risk of genetic drift. Because the pedigree of each cryopreserved embryo is known, one can selectively recover only embryos that are siblings, i.e., derived from the same parents. As a result, the inbred mouse strain is propagated through consecutive brother-sister breeding, keeping the inbred status of the mouse strain intact.

I. Maintaining Genetic Stability Using Cryopreserved Embryos:

The present invention provides methods of maintaining genetic stability of a non-human animal inbred strain. In one embodiment, the method comprises: (1) maintaining a foundation colony of an inbred strain; (2) producing pedigree-tracked stock of cryopreserved embryos derived from the foundation colony; (3) at appropriate intervals, selecting cryopreserved embryos that are inbred breeding pairs, and producing live animals from the embryos; (4) from the animals produced, selecting an inbred breeding pair and use the pair as a new founder pair to produce animals in the strain; and (5) repeating steps (3) to (4) at appropriate intervals. In this manner, genetic drift of the inbred mouse strain is minimized and genetic stability of the strain is effectively maintained The term "genetic stability" as used herein, refers to effectively reduced genetic drift in an inbred strain, as compared to the genetic drift that would occur if the inbred strain is maintained using currently available methods. The effective reduction of genetic drift means reduced genotypic changes in an inbred strain. Depending on where the changes occur in the genome, the genotypic changes may or may not lead to phenotypic changes. For example, a mutation in the non-coding region of the genome will likely result in no change in the phenotype of an animal. Importantly, a mutation that occurs in the foundation stock of a strain maintained under the Genetic Stability program will not persist in the strain, because it will be purged from the entire animal colony upon the thawing of cryopreserved embryos and using them as new foundation stock. Genetic drift may be assessed by examining a variety of indices, including, for example, coat color, biochemical and immunological markers isoenzymes, major histocompatibility complex (MHC), erythrocytic antigens, hemolytic complement (Hc—formerly C5), tail skin grafting, and behavior changes. Genetic drift may also be assessed by examining a variety of molecular markers using any of techniques available in the art, including, for example, two dimensional protein gels, PCR, SNPs, gene expression profiling, and sequencing.

An inbred strain is produced by a managed breeding scheme leading to a reduction in heterozygosity. Acceptable breeding schemes include: parent-offspring breeding and brother-sister breeding. An inbred strain is typically produced by breeding brother with sister for 10 or more consecutive generations. Animals in the $10^{th}$ or a subsequent generation of an inbred strain can be traced to a single ancestral breeding pair. In a preferred embodiment, an inbred strain is produced by breeding brother with sister for 20 or more consecutive generations, and animals in the $20^{th}$ or a subsequent generation can be traced to a single ancestral breeding pair.

The term "inbred breeding pair", as used herein, refers to any breeding pair whose breeding leads to reduced heterozygosity. An inbred breeding pair may be a parent-offspring pair or a brother-sister pair. In a preferred embodiment, the inbred breeding pair is a brother-sister pair. For ease of description, brother-sister pair will be used as illustration throughout the application to describe the present invention. However, a person of ordinary skill in the art will recognize that a parent offspring pair may be substituted for the brother-sister pair in the present application.

a. Maintaining a Foundation Colony of an Inbred Strain

The foundation colony of an inbred mouse strain is maintained using techniques known to one skilled in the art. As used herein, the term "foundation colony" refers to a colony from which all subsequent animals of the strain are derived. A founder pair is an inbred breeding pair, that gives rise to all subsequent animals for a particular strain. Founders are selected from the foundation colony.

A non-human animal preferably is a rodent, such as a rat or a mouse. A non-human animal may also be a hamster, a guinea pig, a horse, a pig, a goat, a sheep, a chicken, a turkey, a primate or any other non-human animal for which an inbred mouse strain is maintained.

Inbred mouse strains include, but are not limited to 129S1, 129T2, 129X1, 129P3, 129P1, A, AKR, BALB/c, C3H, C57BL/10, C57BL/6, C57BLKS, C57BR/cd, C57L, CBA, DBA/1, DBA/2, FVB, MRL, NOD, SJL, SWR, NOR, NZB, NZW, RBF, BUB, I, LP, NON, P, PL, RIIS, SM, C58, ALR, ALS, BPH, BPL, BPN, DDY, EL, KK, LG, MA, NH, NZM2410, NZO, RF, SB, SEA, SI, SOD1, YBR, and all inbred substrains of each of these mouse strains. Accepted mouse strain nomenclature usage requires that each strain is further identified by the addition of a Lab Code at the end of the strain code, the current list of Lab Codes is maintained by the Institute for Laboratory Animal Research which maintains the International Laboratory Code Registry and can be accessed at: dels.nas.edu/ilar/codes.asp The term "substrains" as used herein, refers to colonies within the same mouse strain that are genetically different from each other. A substrain may arise where two colonies of the same inbred strain have been separated for more than 10 generations, or it may arise where there is known genetic difference between separate colonies of the same strain. The genetic difference between different substrains may also be a result of residual heterozygosity in the ancestors at the time of separation which becomes fixed, and/or a result of spontaneous mutation during subsequent generations (genetic drift). Examples of substrains include, but are not limited to, 129S1/SvImJ, 129T2/SvEmsJ, 129X1/SvJ, 129P3/J, A/J, AKR/J, BALB/cByJ, BALB/cJ, C3H/HeJ, C3H/HeOuJ, C3HeB/FeJ, C57BL/10J, C57BL/6J, CBA/CaHN-Btkxid/J, CBA/J, DBA/1J, DBA/1LacJ, DBA/2J, FVB/NJ, MRL/MpJ, NOD/LtJ, SJL/J, SWR/J, NOR/LtJ, NZB/BlNJ, NZW/LacJ, RBF/DnJ, 129S6/SvEvTac, AJTAC, BALB/cAnNTac, BALB/cJBomTac, BALB/cABomTac, C57BL/6NTac, C57BL/6JBomTac, C57BL/10SgAiTac, C3H/HeNTac, CBA/JBomTac, DBA/1JBomTac, DBA/2NTac, DBA/2JBomTac, FVB/NTac, NOD/MrkTac, NZM/AegTac, SJL/JcrNTac, BALB/cAnNCrlBR, C3H/HeNCrlBR, C57BL/6NCrlBR, DBA/2NCrlBR, FVB/NCrlBR, C.B-17/IcrCrlBR, 129/SvPasIcoCrlBR, SJL/JorlIcoCrlBR, A/JolaHsd, BALB/cAnNHsd, C3H/HeNHsd, C57BL/10ScNHsd, C57BL/6NHsd, CBA/JCrHsd, DBA/2NHsd, FVB/NHsd, SAMP1/KaHsd, SAMP6/TaHsd, SAMP8/TaHsd, SAMP10/TaHsd, SJL/JCrHsd, AKR/OlaHsd, BiozziABH/RijHsd, C57BL/6JOlaHsd, FVB/NhanHsd, MRL/MpOlaHsd, NZB/OlaHsd, NZW/OlaHsd, SWR/OlaHsd, 129P2/OlaHsd, and 129S2/SvHsd.

Inbred mouse strains also include all strains produced by any transgenic, knockout or siRNA (small interference RNA) or future genetic manipulation technologies that have been bred brother with sister for ten or more consecutive generations.

b. Producing a Pedigree-Tracked Stock of Cryopreserved Embryos

One aspect of the present invention relates to methods of producing a pedigree-tracked stock of cryopreserved animal embryos derived from a foundation colony, as described herein.

A pedigree-tracked stock is a stock in which the pedigree of each embryo in the stock is known. Pedigrees of the embryos may be tracked by following the family tree of the embryos and recording the family tree information. For example, each embryo may be separately labeled with its pedigree information. Alternatively, sibling embryos may be physically stored and labeled together. The term "sibling embryos" as used herein, refers to embryos that are derived from breeding a single brother-sister pair (or an inbred breeding pair). The cryopreserved embryos may be stored by methods known to those skilled in the art. In one embodiment, cryopreserved embryos are stored in sterile plastic insemination straws. Each straw contains only sibling embryos. A straw may contain one embryo only or it may contain multiple sibling embryos. Alternatively, cryopreserved embryos may be stored in other appropriate containers such as plastic vials or glass ampoules.

Embryos of the pedigree-tracked stock of the present invention may be any stage embryos that can be successfully cryopreserved and recovered to produce live animals. Such embryos include all stages of preimplantation embryos from zygotes to blastocysts. Thus, the embryo of the present invention may be, for example, a one-cell embryo (a zygote), a two-cell embryo, a four-cell embryo, an eight-cell embryo, a morula or a blastocyst. A morula is a spherical mass of cells resulting from cleavage of a one cell embryo; the blastocyst develops from the morula and has a blastocoel and an asymmetrically placed cluster of cells, the inner cell mass.

The term "cryopreserved" as used herein refers to being frozen. The cells, embryos, gametes or pre-gametes of the invention are frozen at temperatures generally lower than 0° C. For example, −80° C. can be used for short term storage, and −196° C. or lower can be used for long term storage. Cells, embryos, gametes or pre-gametes in the invention can be cryopreserved for an indefinite length of time. Methods and tools for cryopreservation are well-known to those skilled in the art. See, e.g., U.S. Pat. No. 5,160,312, entitled "Cryopreservation Process for Direct Transfer of Embryos", Glenister and Hall, "Cryopreservation and rederivation of embryos and gametes", in Mouse Genetics & Transgenics: A Practical Approach, $2^{nd}$ Edition (I Jackson & C Abbott, eds.) Oxford Univ. Press, Oxford, pp. 27-29.

"Embryos derived from a foundation colony" as used herein, includes embryos obtained directly from a founder pair, and embryos obtained from progeny of the founder pair.

The number of embryos needed in a cryopreserved stock depends on many factors, including, for example, the length of time over which a genetic stability program is to be maintained, the frequency with which the cryopreserved stock is used to re-establish a foundation colony, and the efficiency of producing live animals from cryopreserved embryos. These factors will differ among different animal species, and among different strains of the same animal species. For example, mice from different inbred strains are known to vary in the recovery efficiency of cryopreserved embryos.

The number of female animals needed to produce a desired number of embryos will also vary. The number of females needed is inversely correlated with the number of oocytes that can be obtained from each female, the proportion of oocytes that are fertilized and the proportion of embryos that develop to term following embryo transfer. Therefore, the number of females required is a function of the efficiency of each step. High efficiency at each step reduces the total number of females required.

In one embodiment, a pedigree-tracked stock of cryopreserved embryos may be produced by first obtaining embryos from a brother-sister pair (founder pair) of the foundation colony, and then cyropreserving the embryos. Pedigree information is tracked and recorded such that each cryopreserved embryo has an identifiable pedigree. In this embodiment, embryos are produced directly by breeding a founder pair. As a result, the pedigree-tracked stock includes only sibling embryos.

Alternatively, the foundation colony is first expanded to produce sufficient numbers of brother-sister pairs. Thus, in another embodiment, a pedigree-tracked stock of cryopreserved embryos derived from a foundation colony may be produced by: (1) obtaining progeny from the foundation colony such that the progeny comprises appropriate numbers of brother-sister pairs; (2) producing embryos from brother-sister pairs among progeny obtained in (1); and (3) cyropreserving embryos produced in (2). Pedigree information is tracked and recorded such that each cryopreserved embryo has an identifiable pedigree. The pedigree-tracked stock produced in this embodiment comprises embryos derived from breeding more than one brother-sister pairs.

One brother-sister pair is distinct from another pair if either the male or the female is different between the two pairs. For example, male A and female B is different from male A and female C, and from male D and female B. "Progeny" as used herein, refers to generations of animals derived from a founder pair, including, for example, F1, F2, F3 and F4 generations. "Appropriate number of distinct brother-sister pairs" is a number that will generate sufficient numbers of embryos for the purpose of creating a cryopreserved stock to maintain genetic stability of an inbred strain.

Obtaining progeny from a foundation stock may be achieved by breeding techniques known to those skilled in the art, including, for example, natural mating, artificial insemination and in vitro fertilization.

Embryos may be obtained from breeding the brother-sister founder pair. "Breeding" as used herein, means the union of male and female gametes so that fertilization occurs. Such a union may be brought about by mating (copulation) or by in vitro or in vivo artificial means. Artificial means include, but are not limited to, artificial insemination, in vitro fertilization, embryo transfer, intracytoplasmic sperm injection, cloning, in vitro culture of fertilized oocytes and embryo splitting. Any method to produce properly aged embryos may be used.

Artificial insemination is a process of fertilizing female animals by manual injection or application of sperm. In such a procedure, male animals are not required at the time of insemination, sperm was obtained from the animals previously. See Wolfe, 1967, and Sato and Kumura, 2002. When breeding is achieved by natural mating or artificial insemination, embryos may be obtained by flushing the oviduct or uterus of the female after the mating or artificial insemination. See Hogan et al., 2003. The embryo splitting technique is well known to those skilled in the art. Embryo splitting can be carried out by, for example, dividing normal embryos (from 2 cell to morula stage) with a micromanipulator or similar procedure.

In vitro fertilization (IVF) is also well known in the art. See, for example, Hogan et al., Manipulating the Mouse Embryos, A Laboratory Manual, $2^{nd}$ Ed. Page 146-147 (1994). IVF generally comprises collecting oocytes and sperm from a female and a male respectively, fertilizing oocytes from the female with sperm from the male and maintaining the resulting fertilized oocytes under suitable conditions for development of the fertilized oocytes into embryos. Embryos may be harvested at different stages. The female may be superovulated before oocytes are collected for IVF. See, for example, Hogan et al., 2003. As described herein, the oocytes and the sperm are obtained from a brother-sister pair. IVF can be a useful tool to increase the numbers of embryos obtained from a single female.

Intracytoplasmic sperm injection (ICSI) may be used to improve fertilization rate. The ICSI procedure involves removal of the cumulus cells surrounding oocytes and injection of the sperm into the oocytes, ordinarily through a glass pipette. See Kimura and Yanagimachi, 1995.

As an alternative to collecting mature oocytes for IVF from a female, immature oocytes may be obtained and allowed to mature in vitro, a technique known as "in vitro maturation". In mammals, only a small fraction of immature oocytes develop into mature oocytes, and the rest degenerate and die. By isolating immature oocytes from animals and allowing them to mature in vitro, one can obtain many more oocytes suitable for IVF from a given female. Mammalian oocytes are known to undergo maturation in vitro. In the case of mice, cattle and other mammals, in vitro matured oocytes have been fertilized in vitro and given rise to normal healthy offspring when embryos were transferred to an appropriate uterus (Schroeder and Eppig 1984 Dev. Biol. 102:493; Sirard et al. 1988, Biol. Reprod. 39:546). In vitro maturation technique is well known in the art. See, for example, Chiu et al., Effects of Myo-inositol on the in-vitro Maturation and Subsequent Development of Mouse Oocytes, Human Reprod. 18: 408-416 (2003) and O'Brien et al., A Revised Protocol for In Vitro Development of Mouse Oocytes from Primordial Follicles Dramatically Improves Their Developmental Competence, Biol. Reprod. 68: 1682-1686 (2003).

In another alternative, oocytes may be collected from a "host" female into whom a section of ovaries from a desired female had previously been implanted. The desired female is the sister from a brother-sister pair derived from the foundation colony, from whom oocytes are needed for IVF. This is achieved by harvesting ovaries from the sister of a brother-sister pair, sub-dividing the ovaries into sections, implanting each section into an ovarisectomized by surgery host female, or a chemically or genetically compromised host female, and collecting oocytes from each of the host females. This approach results in more oocytes obtained for a given female.

c. Producing Live Animals from Cryopreserved Embryo Stock

At an appropriate time, cryopreserved sibling embryos are selected and live animals are produced from these sibling embryos. In one embodiment, live animals are produced from one set of sibling embryos. In another embodiment, live animals are produced from more than one set of sibling embryos.

Producing live animals from cryopreserved embryos may be carried out using techniques known to those skilled in the art. In one embodiment, live animals are produced from cryopreserved embryos by: (1) thawing the cryopreserved embryos; (2) implanting the thawed embryos into at least one pseudopregnant female recipient; and (3) maintaining the pseudopregnant female recipients under conditions suitable for production of live animals. As a result, live animals are produced.

The term "thawing" as used herein refers to the process of increasing the temperature of cryopreserved materials. Methods of thawing cryopreserved materials, such that they are able to give rise to live animals after the thawing process are well-known to those of ordinary skill in the art.

The term "implanting" as used herein in reference to embryos, refers to the transfer of one or more embryos to a female animal with an embryo described herein. A pseudopregnant female recipient is a female animal whose reproductive tract becomes receptive for transferred embryos even though her own unfertilized eggs degenerate. A pseudopregnant female animal is generated, for example, by mating a female with a sterile male. The technique of implanting a pseudopregnant female is well known to a person of ordinary skill in the art. See, e.g., Recovery, Culture and Transfer of Embryos in Hogan et al., Manipulating the Mouse Embryos, A Laboratory Manual, $2^{nd}$ Ed. page 170-181. The embryos may be allowed to develop in utero or, alternatively, the fetus may be removed from the uterine environment before parturition d. Selecting a New Founder Pair from the Live Animals Produced From the live animals produced in step (c), a brother-sister pair is selected to be a new founder pair to re-establish the foundation colony. All subsequent animals in the mouse strain will be derived from this new founder pair, until the process of using cryopreserved stock to re-establish the foundation colony is repeated, as described in the next section.

A brother-sister pair may be selected randomly as a founder pair. Alternatively, the founder pair may be selected by phenotypic screening, genotypic screening, or a combination of both. Phenotypic screening may be conducted by visual inspection of, for example, coat color and behavior changes. Phenotypic screening may also be conducted by quantitative analysis of muscle grip strength, unrestrained measurements of respiratory rate, tidal volume and other respiratory indices with or without respiratory challenge, simultaneous measurements of $CO_2$ production, $O_2$ uptake, food and water intake, locomotor activity and circadian patterns, clinical chemistry test and blood chemistry test, expression profiling of sampled tissues. Genotypic screening may be conducted by examining a variety of indices, including, for example, biochemical and immunological markers isoenzymes, major histocompatibility complex (MHC), erythrocytic antigens, hemolytic complement (Hc—formerly C5), microsatellites and single nucleotide polymorphisms (SNPs). Genotypic screening can be carried out by any techniques available in the art, including, for example, PCR and sequencing.

e. Repeating Steps (c)-(d)

At an appropriate interval, the process of producing live animals from the pedigree-tracked stock and selecting a brother-sister as a new founder pair is repeated. An "appropriate interval" is an interval used to re-establish a foundation colony using the cryopreserved stock, that results in maintenance of genetic stability of an inbred strain. The appropriate interval can be empirically determined for a strain, such as by assessing the rate of genetic drift in the strain. The appropriate interval thus determined will vary among different inbred animal species and among different strains within the same animal species. Alternatively, an appropriate interval may be a pre-defined interval. An appropriate interval may be any number of generations between 1 and 40, such as, for example, every generation, every 5 generations, every 10 generations, every 20 generations or every 40 generations.

Another aspect of the present invention relates to methods of maintaining genetic stability of an inbred animal strain. The methods include producing live animals from cyropreserved embryos of a pedigree-tracked stock derived from the foundation colony of the inbred strain, using a brother-sister pair selected from the live animals as a new founder pair and repeating the procedure at appropriate intervals.

Still another aspect of the present invention provides pedigree-tracked stocks of cryopreserved embryos derived from a foundation colony. The pedigree-stocks may be produced by any of the methods described herein or any variation of these methods. Such pedigree-tracked cryopreserved embryos may be used to re-establish the foundation colony at appropriate intervals. In one embodiment, the pedigree-tracked cryopreserved embryos includes only embryos obtained by breeding a single brother-sister founder pair. In another embodiment, the pedigree-tracked cryopreserved embryos includes embryos obtained by breeding more than one brother-sister pairs derived from the foundation colony.

A further aspect of the present invention relates to genetically stabilized non-human animal inbred strains made by the methods described herein.

A still further aspect of the present invention provides a business method of supplying non-human animal inbred strains with limited genetic drift. The method includes: (1) maintaining a foundation colony of the inbred strain; (2) producing a pedigree-tracked stock of cryopreserved embryos derived from the foundation colony; (3) at an appropriate time, selecting cryopreserved embryos that are siblings, and produce live animals from the embryos; (4) selecting a brother-sister pair from the animals produced and using them as a new founder pair to derive future animals in the strain; (5) repeating steps (1) to (4) at appropriate intervals and (6) providing animals to customer in response to a customer's order.

II. Maintaining Genetic Stability Using Cryopreserved Gametes or Pre-Gametes Stock As an alternative to using embryos, gametes or pre-gametes derived from a foundation colony of an inbred strain may be used to create a pedigree-tracked stock for the purpose of maintaining the genetic stability of an inbred strain.

Accordingly, the present invention provides methods of maintaining genetic stability of an inbred strain, comprising: (1) maintaining a foundation colony of an inbred strain; (2) producing a pedigree-tracked stock of cryopreserved gametes or pre-gametes derived from the foundation colony; (3) at appropriate intervals, selecting cryopreserved gametes or pre-gametes that are obtained from a single brother-sister pair, and producing live animals from them; (4) selecting a brother-sister pair from the resulting animals and using them as a new founder pair to produce future animals in the strain; and (5) repeating steps (3) to (4) at appropriate intervals.

The term "gamete" as used herein refers to any male or female germ cell that is capable of initiating formation of a new diploid individual. Examples of gametes are sperm and oocytes. Gametes can be present in fluids, tissues, and organs collected from animals (e.g., sperm is present in semen).

The term "pre-gamete" includes any precursors that are capable of giving rise to gametes. Such precursors may be progenitor cells of the gametes. Progenitor cells for sperm include, but are not limited to, primordial germ cells, spermatogonia (including type A1, A2, A3 and A4 spermatogonia), spermatogonial stem cells, intermediate spermatogonium, type B spermatogonia, primary spermatocytes, secondary spermatocytes and spermatids. Progenitor cells for oocyte include, but not limited to, primordial germ cells, oogonia, primary oocytes and secondary oocytes. Such precursors may also be embryonic stem cells, which are capable of giving rise to gametes. See, for example, Hubner et al., Science 300: 1251-6 (2003). The term "pre-gamete" also refers to any cell, tissue or organ capable of giving rise to gametes, including, for example, ovary and testes.

A primordial germ cell is a diploid somatic cell capable of becoming a germ cell. Primordial germ cells can be isolated, for example, from the genital ridge. The genital ridge is a known defined region of the developing embryo, and is well-known to a person of ordinary skill in the art. See, e.g., Strelchenko, 1996, Theriogenology 45: 130-141 and Lavoir 1994, J. Reprod. Dev. 37: 413-424.

One aspect of the present invention relates to methods of producing a pedigree-tracked stock of cryopreserved gametes or pre-gametes derived from a foundation colony.

The number of gametes or pre-gametes necessary to create a pedigree-tracked stock for maintaining genetic stability is determined using the same set of considerations for embryo stocks. Likewise, the number of animals needed to produce sufficient number of gametes or pre-gametes for the stock is determined with the same considerations as in the context of embryo stocks, as discussed above. Thus, gametes or pre-gametes may be obtained from a founder pair directly. Alternatively, as for embryo stocks, the foundation colony is first expanded to produce sufficient numbers of distinct brother-sister pairs and gametes and pre-gametes may then be obtained from these brother-sister pairs.

Gametes and pre-gametes are obtained from brother-sister pairs that are either live animals or embryos. Techniques for obtaining gametes or pre-gametes are known in the art. See, for example, Ogura and Yanagimachi, 1995, and Kubota et al., 2003.

Gametes and pre-gametes may be cryopreserved using any method known in the art. See, for example, U.S. Pat. No. 5,758,763, entitled "Methods for Cryopreservation of Primordial Germ Cells and Germ Cells", U.S. application Ser. No. 20020131957, entitled "Cryopreservation of Sperm", Sztein et al., Biol. Reprod. 58: 1071-1074 (1998) and Candy et al, 2000.

Pedigree-tracked gametes or a pre-gamete stock is a stock in which the pedigree of each gamete or pre-gamete within the stock is known. Pedigrees of the gametes or pre-gametes may be tracked by following their pedigree and recording the pedigree information. For example, each gamete or pre-gamete may be separately labeled with its pedigree information. For another example, gametes or pre-gametes from single individuals may be physically stored and labeled as a sibling group. In this manner, one is able to select only gametes or pre-gametes that are obtained from a single brother-sister future pair. For example, gametes may be stored in a manner enabling one to select only eggs from a particular female and sperm from the female's brother.

At appropriate intervals, one may select cryopreserved gametes or pre-gametes that are obtained from a single brother-sister pair, and produce live animals from them. Cryopreserved pre-gametes may be thawed and cultured under suitable conditions for the pre-gametes to give rise to gametes, which are then undergo in vitro fertilization to produce live animals.

In one embodiment, oocytes are collected from superovulated females and cryopreserved. Sperm are collected from respective male siblings and cryopreserved. At appropriate intervals, oocytes and sperm from siblings are thawed and used to produce embryos by IVF. Resulting embryos are transferred to pseudopregnant recipients to generate offspring.

Another aspect of the present invention relates to methods of maintaining genetic stability of an inbred animal strain. The methods include producing live animals from cyropreserved gametes or pre-gametes of a pedigree-tracked stock derived from the foundation colony of the inbred strain, using a brother-sister pair selected from the live animals as a new founder pair and repeating the procedure at appropriate intervals.

Still another aspect of the present invention provides pedigree-tracked stocks of cryopreserved gametes or pre-gametes derived from a foundation colony. Such pedigree-tracked stock may be used to re-establish the foundation colony at appropriate intervals.

A further aspect of the present invention relates to a genetically stabilized non-human animal inbred strain made by the methods described herein.

A still further aspect of the present invention provides a business method of supplying non-human animal inbred strains with limited genetic drift. The method includes: (1) maintaining a foundation colony of an inbred strain; (2) producing a pedigree-tracked stock of cryopreserved gametes or pre-gametes derived from the foundation colony; (3) at appropriate intervals, selecting cryopreserved gametes or pre-gametes that are obtained from a single brother-sister pair, and producing live animals from them; (4) selecting a brother-sister pair from the resulting animals and using them as a new founder pair to produce future animals in the strain; (5) repeating steps (3) to (4) at appropriate intervals; and (6) providing a mouse to customer in response to customer's order.

III. Maintaining Genetic Stability Using Cryopreserved ES Cell Stock

As an alternative to using embryos, embryonic stem cells derived from a foundation colony of an inbred strain may be used to create a pedigree-tracked stock for the purpose of maintaining the genetic stability of an inbred strain.

Accordingly, the present invention provides methods of maintaining genetic stability of an inbred strain, comprising: (1) maintaining a foundation colony of an inbred strain; (2) producing a pedigree-tracked stock of cryopreserved embryos derived from the foundation colony; (3) at appropriate intervals, selecting cryopreserved embryonic stem cells that are obtained from a single brother-sister pair, and producing live animals from them; (4) selecting a brother-sister pair from the animals produced and using them as a new founder pair to derive future animals in the strain; and (5) repeating steps (3) to (4) at appropriate intervals.

An embryonic stem cell (ES cell) is a pluripotent cell isolated from an embryo. ES cells may be cultured in vitro with or without feeder cells. ES cells can be established from embryonic cells isolated from early embryos, principally from blastocyst stage embryos. The methods for both ES cell establishment and culture are well known to a person of ordinary skill in the art. See, e.g., WO 97/37009, entitled "Cultured Inner Cell Mass Cell-Lines Derived from Ungulate Embryos," Stice and Golueke, published Oct. 9, 1997, and Yang & Anderson, 1992, Theriogenology 38: 315-335, both of which are incorporated herein by reference in their entireties. The term "embryonic stem cell" or "ES cell" as used herein, includes ES cell lines.

ES cells of the pedigree-tracked stock can be obtained from embryos produced by breeding a brother-sister pair of the foundation colony. Such techniques are well-known to those skilled in the art. The ES cells are then cryopreserved and stored in a manner to allow one to select only ES cells obtained from a single brother-sister pair. Preferably, the ES cells are cyropreserved at an early passage, such as, for example, within 3-20 passages.

The number of frozen units of ES cells necessary to create a pedigree-tracked stock for maintaining genetic stability depends on many factors, including, for example, the length of time over which a genetic stability is to be maintained, the frequency with which the cryopreserved stock is used to re-establish a foundation colony, the efficiency of producing live animals from cryopreserved ES cells and the efficiency of the ES cells to give rise to live animals that are derived completely from the ES cells. These factors will differ not only among different animal species, but among different strains of the same animal species.

ES cells may be obtained from embryos resulted from breeding a founder pair. Alternatively, the foundation colony is first expanded to produce sufficient numbers of distinct brother-sister pairs and ES cells may then be obtained from embryos resulted from breeding these brother-sister pairs.

ES cells may be cryopreserved using method known to those skilled in the art. See, for example, Hogan et al., 2003.

Cryopreserved ES cells of the pedigree-tracked stock can be thawed and used to re-establish a foundation colony at appropriate intervals. In one embodiment, ES cells derived from a male and a female (brother-sister) embryo are introduced separately into a morula or blastocyst stage embryo and allowed to participate in the development of the animal. The resulting offspring are typically chimeras, with portions of the chimera developed from either host embryo or the contributing male or female ES cells. The germline of the chimera could contain derivatives of both the host and the contributing ES cells. By the use of coat color and/or other genetic markers, one can select offspring which are completely derived from the ES cells used. The resulting offspring can then be used to re-establish the foundation colony.

In an alternative embodiment, male ES cells and female ES cells of the pedigree-tracked stock are separately aggregated with a tetraploid host embryo (tetraploid embryo complementation), which may be made by fusion of the two cell stage embryos with, for example, an electrical pulse. Such ES cells will successfully fully colonize the mouse embryo, while the extra embryonic tissue are supplied by the tetraploid host. This will give rise to offspring that are completely derived from either the male ES cells or the female ES cells, depending on the ES cells used to aggregate with the tetraploid host embryo. Appropriate monitoring of the process using coat color and/or other genetic markers can distinguish any possible host-embryo-derived offspring from those derived from the ES cells. One can thus select offspring derived completely from each ES cell. A brother-sister pair may then be selected from the offspring derived from the male ES cell (brother) and the offspring from the female ES cell (sister) to re-establish the foundation colony.

Such techniques are known in the art. See, for example, Hogan et al., 2003. Derivation of completely cell culture-derived mice from early-passage embryonic stem cells, Proc Natl Acad Sci USA. 90, 8424-8428. See also www.mshri-.on.ca/nagy/diploid/diploid.htm, and www.mshri.on.ca/nagy/Tetraploid/tetra.htm In a further embodiment, male and female offspring can be produced from a single male ES cell line of the pedigree-tracked stock. The male ES cells contain an X chromosome and a Y chromosome (XY). It has been shown that Y chromosome is lost at a high frequency in subclones of the XY cell lines, making it routine to identify XO cells in the subclones of the XY ES cell line. These XO ES cells can be used to produce female offsprings that are fertile via either tetraploid embryo complementation or chimera formation (See Eggan et al., 2002). One of the female offspring can be selected to breed with one of the male offspring derived from the male ES cells (XY) to re-establish the foundation colony.

ES cells are known to be able to form germ cells in vitro. See Toyooka, Y. et al., 2003. Thus, in another embodiment, ES cells of the pedigree-tracked stock are used to give rise to germ cells in vitro, which are then used to give rise to offspring derived from the ES cells.

Another aspect of the present invention relates to methods of producing a pedigree-tracked stock of cryopreserved ES cells derived from a foundation colony.

A further aspect of the present invention relates to methods of maintaining genetic stability of an inbred mouse strain. The methods include five steps: (1) from a pedigree-tracked cryopreserved ES cells stock derived from the foundation colony of the inbred strain, selecting cryopreserved ES cells that are obtained from a single brother-sister pair and producing live animals from these ES cells; (2) from the live animals so produced, selecting a brother-sister pair as a new founder pair; and (3) repeating steps (1)-(2) at appropriate intervals.

Another aspect of the present invention provides pedigree-tracked stocks of cryopreserved ES cells derived from a foundation colony. Such pedigree-tracked stock may be used to re-establish the foundation colony at appropriate intervals.

A further aspect of the present invention provides a business method of supplying non-human animal inbred strain with limited genetic drift. The method comprises: (1) maintaining a foundation colony of the inbred strain; (2) producing a pedigree-tracked stock of cryopreserved ES cells derived from the foundation colony; (3) at an appropriate time, select cryopreserved ES cells that are obtained from a single brother-sister pair, and produce live animals from them; (4) out of the live animals produced, select a brother-sister pair and use them as a new founder pair to derive future animals in the strain; (5) repeating steps (1) to (4) at appropriate intervals; and providing an animal in response to the customer's order.

The practice of the present invention will employ, unless otherwise indicated, conventional techniques of mouse genetics, developmental biology, cell biology, cell culture, molecular biology, transgenic biology, microbiology, recombinant DNA, and immunology, which are within the skill of the art. Such techniques are described in the literature. See, for example, Current Protocols in Cell Biology, ed. by Bonifacino, Dasso, Lippincott-Schwartz, Harford, and Yamada, John Wiley and Sons, Inc., New York, 1999, Manipulating the Mouse Embryos, A Laboratory Manual, $3^{rd}$ Ed., by Hogan et al., Cold Spring Harbor Laboratory Press, Cold Spring Harbor, N.Y., 2003, Gene Targeting: A Practical Approach, IRL Press at Oxford University Press, Oxford, 1993, and Gene Targeting Protocols, Human Press, Totowa, N.J., 2000. All patents, patent applications and references cited herein are incorporated in their entirety by reference.

EXEMPLIFICATION

The invention now being generally described will be more readily understood by reference to the following examples, which are included merely for purposes of illustration of certain aspects and embodiments of the present invention, and are not intended to limit the invention.

Example 1

Maintaining the Genetic Stability of an Inbred Strain Using Embryo Stock

The FIGURE depicts a scheme for creating a pedigree-tracked stock of cryopreserved embryos derived from a foundation colony to be used to maintain genetic stability. This is only one embodiment of the present invention. The left panel in the FIGURE shows the first step: a founder pair (the P generation) is selected and bred several times to generate multiple litters. In the scheme represented, six sisters and two brothers (F1 generation) are picked for the next step. The middle panel of the FIGURE shows the second step: Each F1 generation sister is separately caged in order for their litters to be tracked. In the scheme shown, the same male is mated in rotation with a group of three F1 generation sisters. Each of the six F1 generation sisters will be mated multiple times with their respective brother to produce multiple litters of F2 generation. The right panel of the FIGURE shows the third step: nine F2 generation sisters and one brother derived from a single F1 generation sister will be used in IVF to produce embryos. IVF is performed for each of the 6 or more sets of about 9 sisters and one brother. Embryos from each of the 54 females (6×9) are cryopreserved in an individual straw. This will give more than two fold redundancy covering 25 years plus and includes embryos for controls and/or unforeseen eventualities.

At appropriate intervals, sibling embryos from the cryopreserved stock are thawed and transferred to a pseudopregnant female recipient to generate offspring. A brother-sister pair is then selected from the offspring as a new founder pair to re-establish the foundation colony.

A person with ordinary skill in the art will understand that what described above merely represents one embodiment for producing a pedigree-tracked cryopreserved embryo stock of the present invention. Clearly, many of the details of the scheme can vary, including, for example, the number of generations needed to expand the foundation colony before making the embryo stock, the number of females used per generation and the type of the inbred breeding pair used. For example, one may select a breeding pair and produce F(x+1) offspring (where x is the generation number at the time of selection) from the breeding pair. In the meantime, sperm from the male of the breeding pair are obtained and cryopreserved in aliquots. Female F(x+1) offspring may be bred by IVF with the thawed sperm (parent-offspring breeding) to produce F(x+2) embryos that can be cryopreserved to produce pedigree-tracked stock.

Example 2

Maintaining the Genetic Stability of an Inbred Strain Using Gametes Stock

In one embodiment, female mice derived from a foundation colony are superovulated and oocytes are collected and cryopreserved. Sperm from a respective male sibling of the females are also collected and cryopreserved. At appropriate intervals, oocytes and sperm from siblings are thawed and used to produce embryos by IVF. Resulting embryos are transferred to pseudopregnant recipients to yield offspring. A brother-sister pair is then selected from the offspring as a new founder pair to re-establish the foundation colony.

Example 3

Maintaining the Genetic Stability of an Inbred Strain Using Pre-Gametes Stock

Cryopreserved Ovaries and Sperm

Ovaries from females derived from a foundation colony are cryopreserved as are sperm from their respective male siblings. At desired intervals, the ovaries are thawed and transferred. Once fertility of the recipient female has been demonstrated, she is superovulated and artificially inseminated using cryopreserved sperm from one of her siblings to produce offspring. A brother-sister pair is then selected from the offspring as a new founder pair to re-establish the foundation colony.

Cryopreserved Ovaries and Spermatogonial Stem Cells

Ovaries are collected and cryopreserved as above. Spermatogonial stem cells are collected from the male siblings and cryopreserved. Spermatogonial stem cells are thawed and transplanted at appropriate intervals to produce fertile males. Once fertility of the male has been demonstrated, ovaries from his female siblings are thawed and transplanted. The animals are then mated to produce offspring. A brother-sister pair is then selected from the offspring as a new founder pair to re-establish the foundation colony. See Candy et al., 2000, and Nagano and Brinster 1998.

Example 4

Maintaining the Genetic Stability of an Inbred Strain Using ES Cell Stock

Male and female ES cells are isolated from an inbred, pedigreed bother-sister mating and cryopreserved. At appropriate interval, the male and female ES cells derived from a brother-sister mating are recovered from storage. Host embryos are prepared from a genetically different strain, e.g. different coat color from the ES cells, and induced to fuse via an electrical pulse yielding a tetraploid embryo. The surviving embryos are cultured to morula stage. Multiple groups of male ES cells (1-40 cells) are placed in close proximity to one of the tetraploid host embryos. Likewise, multiple groups of female ES cells (1-40 cells) are placed in close proximity to the other tetraploid host embryo. After the ES cells and their respective tetraploid embryo have coalesced to a single embryo (overnight culture), the embryos are introduced into a pseudopregnant female recipient. After birth appropriate coat color and/or other genetic markers can be used to select offspring that are derived from the ES cells. Brother-sister pairing can then be made using these offspring to re-establish the foundation colony.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The methods, embryo stocks and gamete stocks are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

It should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

Candy C J, Wood M J, Whittingham D G. 2000. Restoration of a normal reproductive lifespan after grafting of cryopreserved mouse ovaries. Hum Reprod. June; 15(6):1300-4.

Chiu et al., Effects of Myo-inositol on the in-vitro Maturation and Subsequent Development of Mouse Oocytes, Human Reprod. 18: 408-416 (2003)

Eggan, K. et al. (2002). "Male and female mice derived from the same embryonic stem cell clone by tetraploid embryo complementation." Nat Biotechnol 20(5): 455-9.

Glenister and Hall, "Cryopreservation and rederivation of embryos and gametes" in Mouse Genetics & Transgenics: A Practical Approach, $2^{nd}$ Edition (I Jackson & C Abbott, eds.) Oxford Univ. Press, Oxford, pp. 27-59.

Han M S; Niwa K; Kasai M, Vitrification of rat embryos at various developmental stages. Theriogenology 2003 Apr. 15; 59(8):1851-63

Hogan, B., Beddington, R., Costantini, F., Lacy, E. Manipulating the Mouse Embryos, A Laboratory Manual, $3^{rd}$ Ed., Cold Spring Harbor Laboratory Press, Cold Spring Harbor, N.Y., 2003, Hubner et al., Derivation of oocytes from mouse embryonic stem cells, Science 300: 1251-6 (2003).

Kimura and Yanagimachi, Intracytoplasmic sperm injection in the mouse, Biol. Reprod. 52: 709-20, 1995.

Kimura and Yanagimachi, Development of normal mice from oocytes injected with secondary spermatocyte nuclei, Biol. Reprod. 53: 855-62, 1995

Kimura and Yanagimachi, Mouse oocytes injected with testicular spermatozoa or round spermatids can develop into normal offspring, Development 121: 2397-405, 1995.

Kubota, Avarbock and Brinster, Spermatogonial stem cells share some, but not all, phenotypic and functional characteristics with other stem cell, Proc. Nat. Acad. Sci. 100: 6487-6492, 2003.

Lavoir et al., Isolation and identification of germ cells from fetal bovine ovaries. Molecular Reprod. Dev. 37: 413-424 (1994).

Nagano M, Brinster R L. 1998. Spermatogonial transplantation and reconstitution of donor cell spermatogenesis in recipient mice. APMIS. January; 106(1):47-55; discussion 56-7.

Nagy, A.; Rossant, J.; Nagy, R.; Abramownewerly, W.; Roder, J. C. (1993). Derivation of completely cell culture-derived mice from early-passage embryonic stem cells, Proc Natl Acad Sci USA. 90, 8424-8428.

O'Brien et al., A Revised Protocol for In Vitro Development of Mouse Oocytes from Primordial Follicles Dramatically Improves Their Developmental Competence, Biol. Reprod. 68: 1682-1686 (2003).

Ogura and Yanagimachi, Spermatids as male gametes, Reprod. Fertil. Dev. 7: 158-9, 1995

Sato M, Kimura M. 2002. Comparison of intrabursal transfer of spermatozoa, a new method for artificial insemination in mice, with intraoviductal transfer of spermatozoa.

J Assist Reprod Genet. November; 19(11):523-30.

Schroeder and Eppig 1984 Dev. Biol. 102:493

Sirard et al. 1988, Biol. Reprod. 39:546

Specht and Schoepfer, Deletion of the alpha-synuclein locus in a subpopulation of C57BL/6J inbred mice, BMC Neurosci. 2, 11 (2001).

Strelchenko, Bovine Pluripotent stem cells, Theriogenology 45: 130-141 (1996)

Sztein, J M, Noble K, Farley J S, Mobraaten L E. 2001. Comparison of permeating and nonpermeating cryoprotectants for mouse sperm cryopreservation. Cryobiology 42 (1):28-39.

Sztein et al., Biol. Reprod. 58: 1071-1074 (1998)

Toyooka, Y., N. Tsunekawa, et al. (2003). Embryonic stem cells can form germ cells in vitro, Proc Natl Acad Sci USA 100(20): 11457-62.

Wolfe H G. 1967. Artificial insemination of the laboratory mouse (*Mus musculus*). Lab Anim Care. 1967 August; 17(4):426-32.

Wotjak, C57Black/Box? The importance of exact mouse strain nomenclature, Trends in Genetics 19: 183-184 (2003).

Yang & Anderson, 1992, Theriogenology 38: 315-335

U.S. Pat. No. 5,758,763, entitled "Methods for Cryopreservation of Primordial Germ Cells and Germ Cells"

U.S. Application No. 20020131957, entitled "Cyropreservation of Sperm"

U.S. Pat. No. 5,160,312, entitled "Cryopreservation Process for Direct Transfer of Embryos"

WO 97/37009, entitled "Cultured Inner Cell Mass Cell-Lines Derived from Ungulate Embryos," Stice and Golueke, published Oct. 9, 1997

What is claimed is:

1. A method of maintaining genetic stability of an inbred rodent strain, comprising:
   (a) establishing a foundation colony of an inbred rodent strain, wherein the foundation colony comprises only brother-sister pairs, parent-offspring pairs or brother-sister pairs and parent-offspring pairs from which all subsequent rodents of the strain are derived;
   (b) maintaining a pedigree-tracked stock of cryopreserved rodent gametes or pre-gametes, wherein the cryopreserved rodent gametes or pre-gametes are obtained from a brother-sister pair or a parent-offspring pair from the foundation colony established in step (a);
   (c) thawing and transplanting cryopreserved pedigree-tracked stock pre-gametes obtained in step (b) to produce pedigree-tracked male and/or female gametes;
   (d) breeding the pedigree-tracked male and female gametes obtained in step (b) and/or (c) to produce pedigree-tracked embryos;
   (e) producing live rodents from pedigree-tracked embryos obtained in step (d);
   (f) selecting a pedigreed inbred breeding pair from the live rodents obtained in step (e) to be used as a new founder pair to re-establish the foundation colony, wherein the inbred breeding pair is a brother sister pair or a parent-offspring pair from which all subsequent rodents of the strain are derived;
   (g) breeding the new founder pair obtained in step (f) to produce offspring and thereby re-establish the foundation colony wherein the foundation colony comprises only brother-sister pairs, parent-offspring pairs or brother-sister pairs and parent-offspring pairs from which all subsequent rodents of the strain are derived; and
   (h) replenishing the foundation colony by repeating steps (c) to (g) at intervals of 1 to 20 generations and thus, inhibiting the accumulation of genotypic changes, thereby maintaining genetic stability of the inbred strain.

2. The method of claim 1, wherein live animals are produced from gametes or pre-gametes obtained from a single brother-sister pair.

3. The method of claim 1, wherein the rodent is mouse.

4. The method of claim 1, wherein the step of maintaining a pedigree-tracked stock of cryopreserved rodent gametes or pre-gametes derived from the foundation colony, comprises:
   (a) obtaining progeny from a foundation stock of the rodent strain, wherein the progeny comprises appropriate numbers of brother-sister pairs;
   (b) producing gametes or pre-gametes from brother-sister pairs;
   (c) cryopreserving gametes or pre-gametes produced in (b), thereby producing a cryopreserved gametes or pre-gametes stock;
   wherein the pedigree of each gamete or pre-gamete in the stock is tracked such that each cryopreserved gamete or pre-gamete has an identifiable pedigree, thereby producing a cryopreserved rodent gamete or pre-gamete stock.

5. The method of claim 4, wherein the rodent is mouse.

6. A method of maintaining genetic stability of inbred mouse strain, comprising:
   (a) establishing a foundation colony of an inbred mouse strain, wherein the foundation colony comprises only brother-sister pairs, parent-offspring pairs or brother-sister pairs and parent-offspring pairs from which all subsequent mice of the strain are derived;
   (b) maintaining a pedigree-tracked stock of cryopreserved mouse embryonic stem cells, wherein the cryopreserved mouse embryonic stem cells are obtained from a brother-sister pair or a parent-offspring pair from the foundation colony established in step (a);

(c) thawing pedigree-tracked cryopreserved mouse embryonic stem cells obtained in step (b) and introducing the stem cells into host embryos to produce pedigree-tracked male and female gametes;

(d) breeding the pedigree-tracked male and female gametes obtained in step (c) to produce pedigree-tracked embryos;

(e) producing live mice from pedigree-tracked embryos obtained in step (d);

(f) screening the live mice to identify mice that are completely derived from the embryonic stem cells;

(g) selecting a pedigreed inbred breeding pair from the live mice identified in step (f) to be used as a new founder pair to re-establish the foundation colony, wherein the inbred breeding pair is a brother sister pair or a parent-offspring pair from which all subsequent mice of the strain are derived;

(h) breeding the new founder pair obtained in step (d) to produce offspring and thereby re-establish the foundation colony wherein the foundation colony comprises only brother-sister pairs, parent-offspring pairs or brother-sister pairs and parent-offspring pairs from which all subsequent mice of the strain are derived; and (i) replenishing the foundation colony by repeating steps (c) to (h) at intervals of 1 to 20 generations and thus, inhibiting the accumulation of genotypic changes, thereby maintaining genetic stability of the inbred strain.

7. The method of claim 6, wherein live animals are produced from embryonic stem cells obtained from a single brother-sister pair.

8. The method of claim 6, wherein the step of maintaining a pedigree-tracked stock of cryopreserved mouse embryonic stem cells derived from a foundation colony, comprises:

(a) obtaining progeny from a foundation stock of a mouse strain, wherein the progeny comprises appropriate numbers of brother-sister pairs;

(b) producing embryonic stem cells from brother-sister pairs;

(c) cryopreserving embryonic stem cells produced in (b), thereby producing a cryopreserved embryonic stem cell stock;

wherein the pedigree of each embryonic stem cell in the stock is tracked such that each embryonic stem cell has an identifiable pedigree, thereby producing a cryopreserved mouse embryonic stem cells stock.

9. The method of claim 1, wherein the cryopreserved rodent gametes are obtained from one or more male rodents and the cryopreserved rodent pre-gametes are obtained from one or more female rodents of one or more brother-sister pairs or parent-offspring pairs.

10. The method of claim 1, wherein the cryopreserved rodent pre-gametes are obtained from one or more male rodents and the cryopreserved rodent gametes are obtained from one or more female rodents of one or more brother-sister pairs or parent-offspring pairs.

11. The method of claim 9, wherein the cryopreserved gametes obtained are sperm and the cryopreserved pre-gametes obtained are ovaries.

12. The method of claim 9, wherein the cryopreserved gametes obtained are sperm and the cryopreserved pre-gametes obtained are primary oocytes, secondary oocytes or female primordial germ cells.

13. The method of claim 1, wherein the cryopreserved rodent pre-gametes are obtained from one or more brother-sister pairs or parent-offspring pairs.

14. The method of claim 1, wherein the cryopreserved pre-gametes obtained are spermatogonial stem cells and ovaries.

15. The method of claim 6, wherein male and female live mice are produced from a single male cryopreserved embryonic stem cell line of the pedigree-tracked stock obtained in step (b).

16. The method of claim 15, wherein female live mice are produced from XO cells identified from the single male pedigree-tracked embryonic stem cell line.

\* \* \* \* \*